United States Patent [19]

Aoki et al.

[11] Patent Number: 4,561,877
[45] Date of Patent: Dec. 31, 1985

[54] DERIVATIVES OF TETRAHYDROBENZOTHIAZOLE AND HERBICIDAL COMPOSITIONS CONTAINING THE SAME AS ACTIVE INGREDIENT

[75] Inventors: Katsumichi Aoki; Takafumi Shida; Hideo Arabori; Satoru Kumazawa; Susumu Shimizu; Takeo Watanabe; Yohichi Kanda; Keigo Satake; Shiro Yamazaki; Hiroyasu Shinkawa; Tsuneaki Chida, all of Iwaki, Japan

[73] Assignee: Kureha Kagaku Kogyo Kabushiki Kaisha, Tokyo, Japan

[21] Appl. No.: 596,927

[22] Filed: Apr. 5, 1984

[30] Foreign Application Priority Data

Apr. 8, 1983 [JP] Japan .................................. 58-61925

[51] Int. Cl.$^4$ ...................... A01N 43/54; A01N 43/66; A01N 43/78; C07D 417/04
[52] U.S. Cl. ............................................ 71/90; 71/92; 71/93; 544/67; 544/68; 544/220; 544/310; 544/316
[58] Field of Search ................. 71/90, 92, 93; 544/67, 544/68, 220, 310, 316

[56] References Cited

U.S. PATENT DOCUMENTS

| | | | |
|---|---|---|---|
| 3,696,101 | 10/1972 | Litt et al. | 71/90 |
| 3,932,410 | 1/1976 | Krenzer | 71/90 |
| 3,951,976 | 4/1976 | Krenzer | 71/90 |
| 3,988,143 | 10/1976 | Krenzer | 71/90 |
| 4,006,009 | 2/1977 | Krenzer | 71/90 |
| 4,040,812 | 8/1977 | Krenzer | 71/90 |
| 4,289,524 | 9/1981 | Belkind | 71/90 |
| 4,481,027 | 11/1984 | Aoki et al. | 71/90 |

Primary Examiner—Henry R. Jiles
Assistant Examiner—J. G. Mullins
Attorney, Agent, or Firm—Austin R. Miller

[57] ABSTRACT

Disclosed herein are a derivative of tetrahydrobenzothiazole represented by the formula (I):

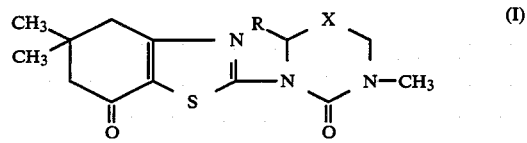

wherein R represents a hydrogen atom, a hydroxyl group or a lower acyloxy group such as acetoxy group and propionyloxy group and X represents a methylene group, $C_1$ to $C_4$-alkylamino group, benzylamino group or —O—, and a herbicidal composition containing the same as an active ingredient.

10 Claims, 11 Drawing Figures

DERIVATIVES OF TETRAHYDROBENZOTHIAZOLE AND HERBICIDAL COMPOSITIONS CONTAINING THE SAME AS ACTIVE INGREDIENT

DETAILED DESCRIPTION OF THE INVENTION

The present invention relates to a derivative of tetrahydrobenzothiazole represented by the formula (I):

wherein R represents a hydrogen atom, a hydroxyl group, a lower acyloxy group such as acetoxy group and propionyloxy group and X represents a methylene group, $C_1$ to $C_4$-alkylamino group, benzylamino group or —O—, and a herbicidal composition containing the same as an active ingredient.

The present inventors have studied for finding out a compound showing an excellent activity in selectively controlling weeds such as Echinochloa crus-galli, Poa annua, Cardamine flexuosa, Portulaca orelacea, etc. without giving any phytotoxicity to crop plants such as rice, wheat, soy-bean and maize, and as a result, they have found that a derivative of tetrahydrobenzothiazole represented by the formula (I) shows an excellent herbicidal activity for practically controlling the weeds, and have attained to the present invention.

The compounds represented by the formula (I) are novel compounds, and of course, the physiological properties of the compounds have never been known. According to the herbicidal tests consisting essentially of foliar application and soil treatment, each of the derivatives of tetrahydrobenzothiazole according to the present invention (hereinafter referred to as "the present compounds") shows an excellent herbicidal activity on broad-leaved weeds, for instance, Stellaria media, Cardamine flexuosa and Portulaca oleracea, Cyperaceous weeds, for instance, Cyperus iria and Gramineous weeds, for instance, those belonging to the genus Echinochloa and Poa annua and particularly shows strong herbicidal activity when applied on leaves and stems of these weeds. The application is carried out on arable lands such as paddy fields, upland fields, orchards, etc. and also on non-arable lands.

In a first aspect of the present invention, there is provided a derivative of tetrahydrobenzothiazole represented by the formula (I):

wherein R represents a hydrogen atom, a hydroxy group or lower acyloxy group such as acetoxy group and propionyloxy group and X represents a methylene group, $C_1$ to $C_6$-alkylamino group, benzylamino group or —O—.

In a second aspect of the present invention, there is provided a herbicidal composition comprising as an active ingredient at least one derivative of tetrahydrobenzothiazole represented by the formula (I).

In the attached Drawing.

The present compounds represented by the formula (I) are synthesized from the compound represented by the formula (II) or the compound represented by the formula (III).

Namely, 2 moles of formaldehyde and 1 mol of a $C_1$ to $C_4$-alkylamine, or 1 mol of benzylamine are reacted with 1 mol of the compound represented by the formula (II) to obtain the compound represented by the formula (I) wherein R represents a hydrogen atom and X represents a $C_1$ to $C_4$-alkylamino or a benzylamino group as follows.

wherein $R^1$ represents a $C_1$ to $C_4$-alkyl- or benzyl group.

In the case where trioxane is reacted with the compound represented by the formula (II) in the presence of an acid catalyst, the compound represented by the formula (I) wherein R represents a hydrogen atom and X represents —O— is obtained as follows.

Also, in the case where the compound represented by the formula (III) is treated with an aqueous dilute solution of a mineral acid, the compound represented by the formula (VI) is obtained, and the thus obtained compound is converted to the compound represented by the formula (VII).

The compound represented by the formula (II) is easily available by reacting the compound represented by the formula (IV) with methyl isocyanate as follows.

The compound represented by the formula (III) is easily synthesized by reacting (3,3-diethoxypropyl)methylamine with a carbamate represented by the formula (V) which is obtained by reacting phenyl chloroformate with the compound represented by the formula (IV) as follows.

The concrete examples of the present compounds and the physicochemical properties thereof are shown in Table 1.

TABLE 1

Figure 1:
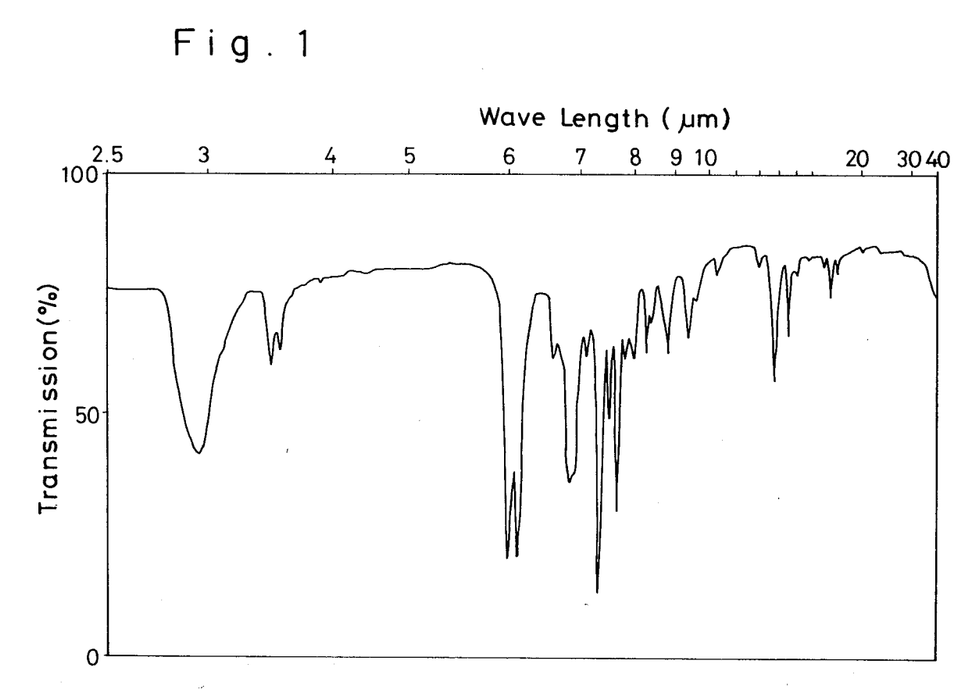
FIGS. 1 to 11 show the infrared absorption spectra of Compounds Nos. 1 to 11 according to the present invention, respectively.
Figure 2:
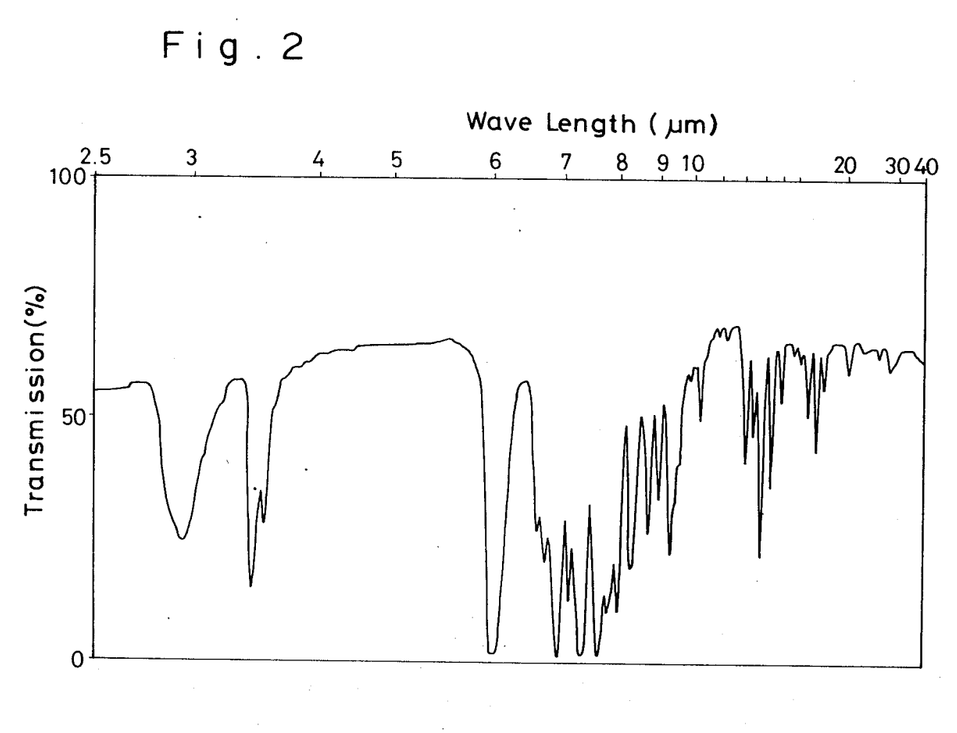

| Compound number | R, X structure | Melting point (°C.) | Yield (%) | Infrared absorption spectrum |
|---|---|---|---|---|
| 1 | CH₃ substituent | 182–184 | 80 | FIG. 1 |
| 2 | CH₂CH₃ substituent | 153–155 | 84 | FIG. 2 |

TABLE 1-continued

Structure header:
R–CH(–X)... with ring: –N(–C(=O)–)N–CH₃

Figure 3:
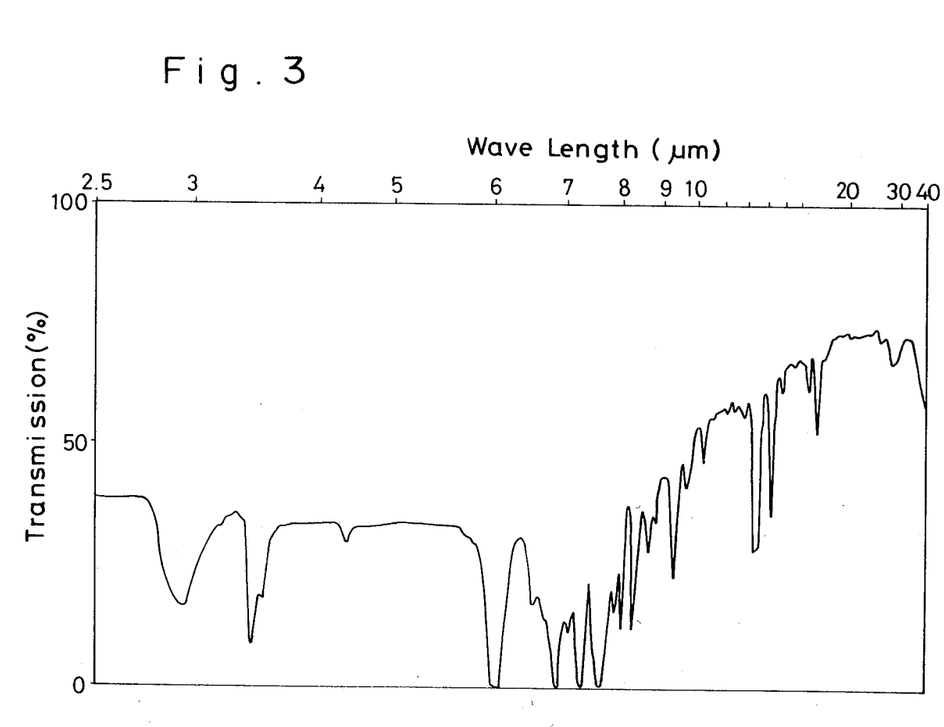
Figure 4:
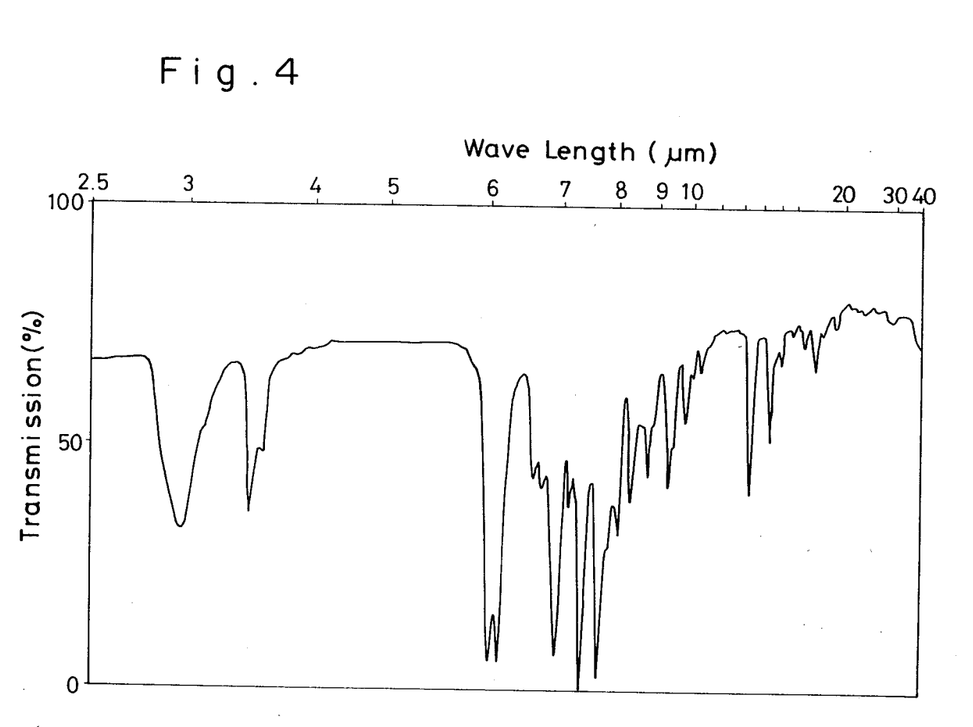
Figure 5:
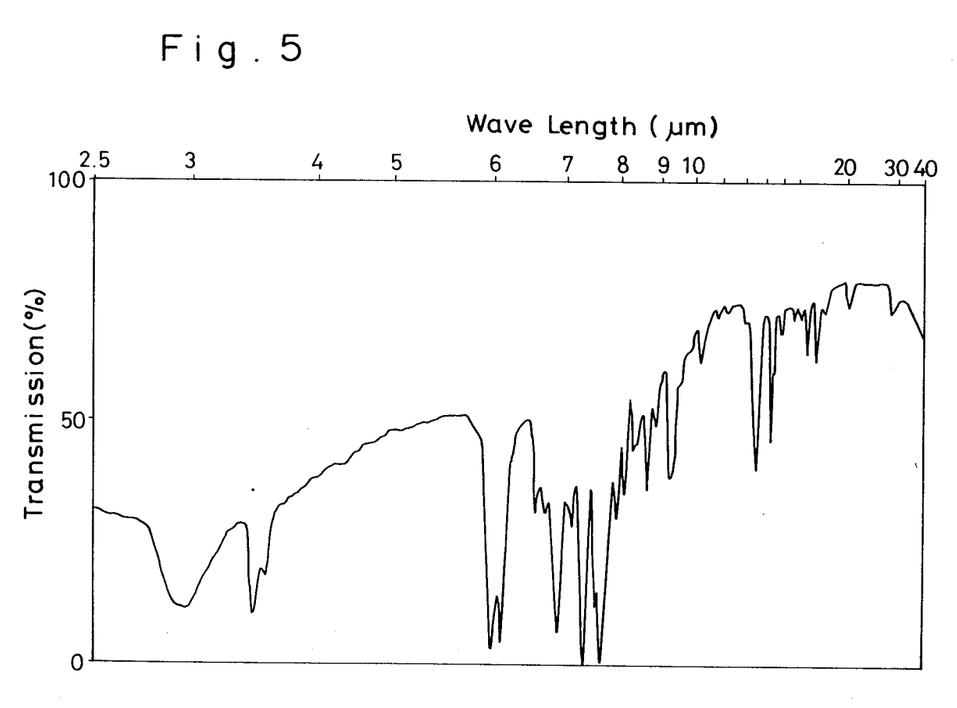
Figure 6:
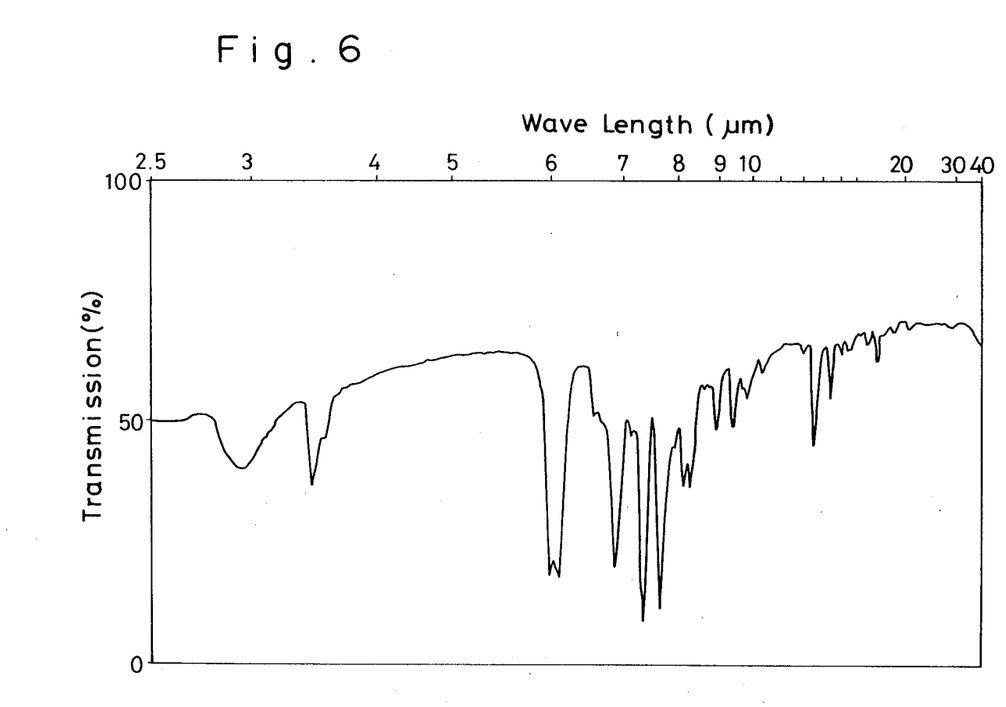
Figure 7:
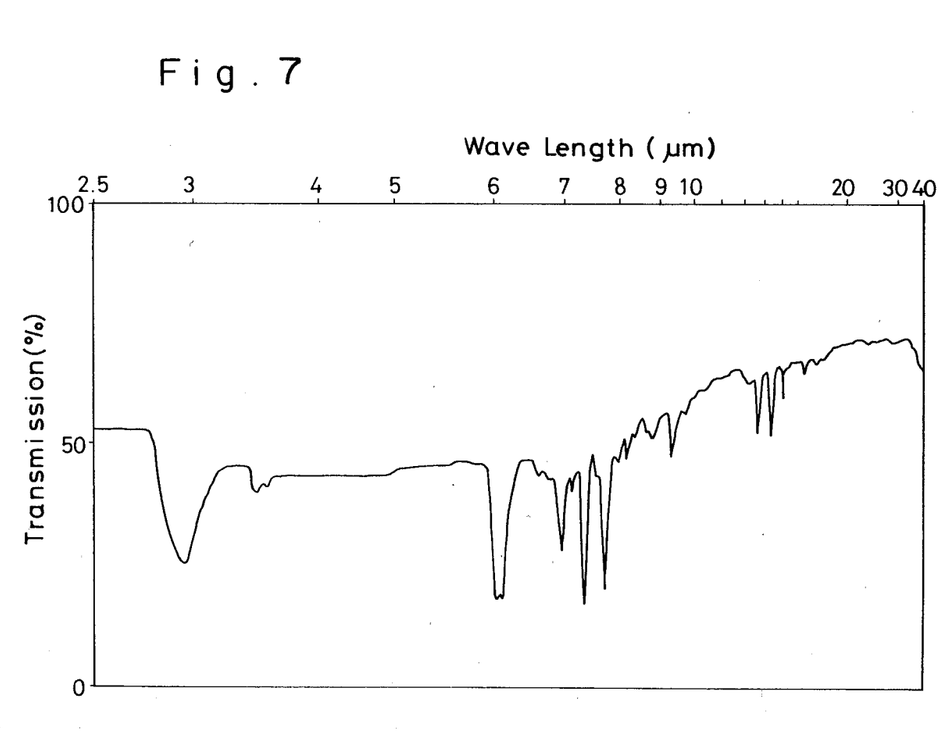
Figure 8:
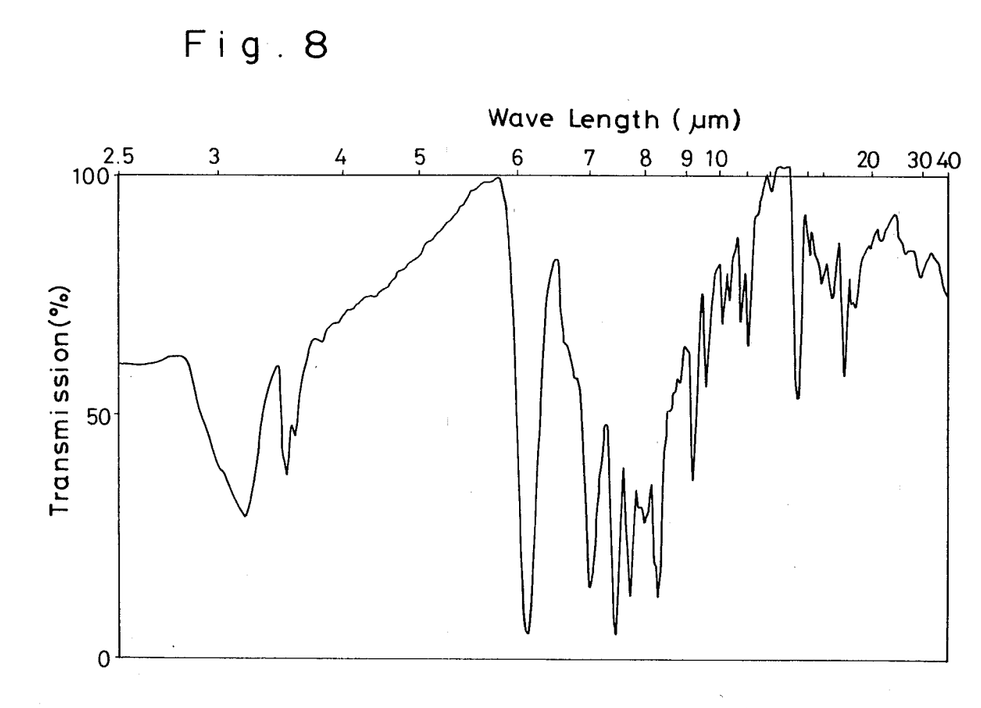
Figure 9:
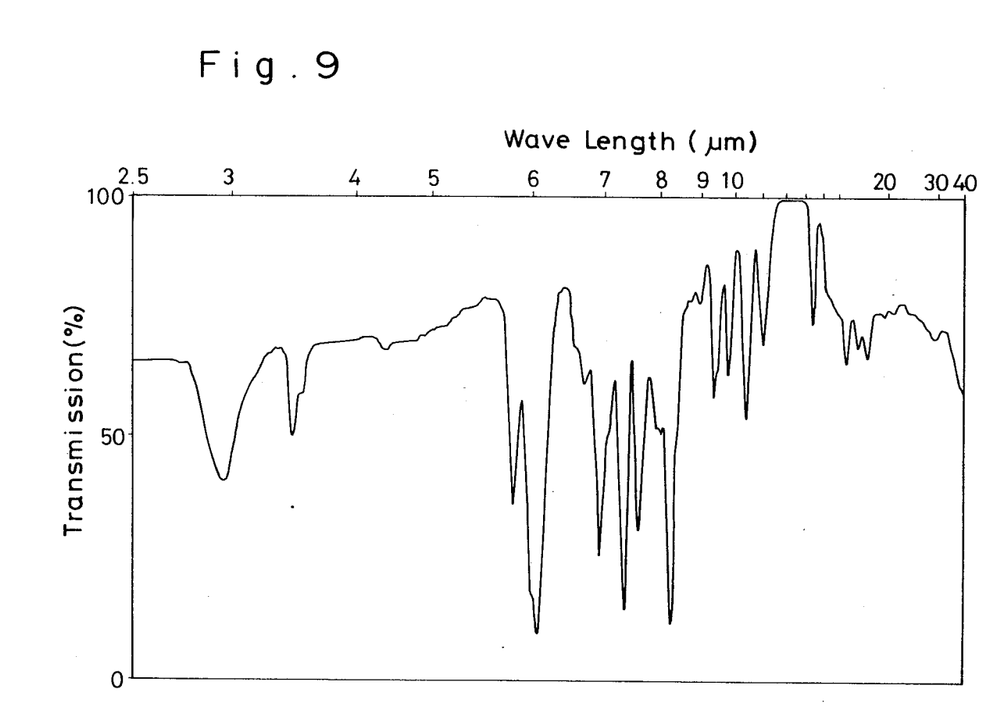
Figure 10:
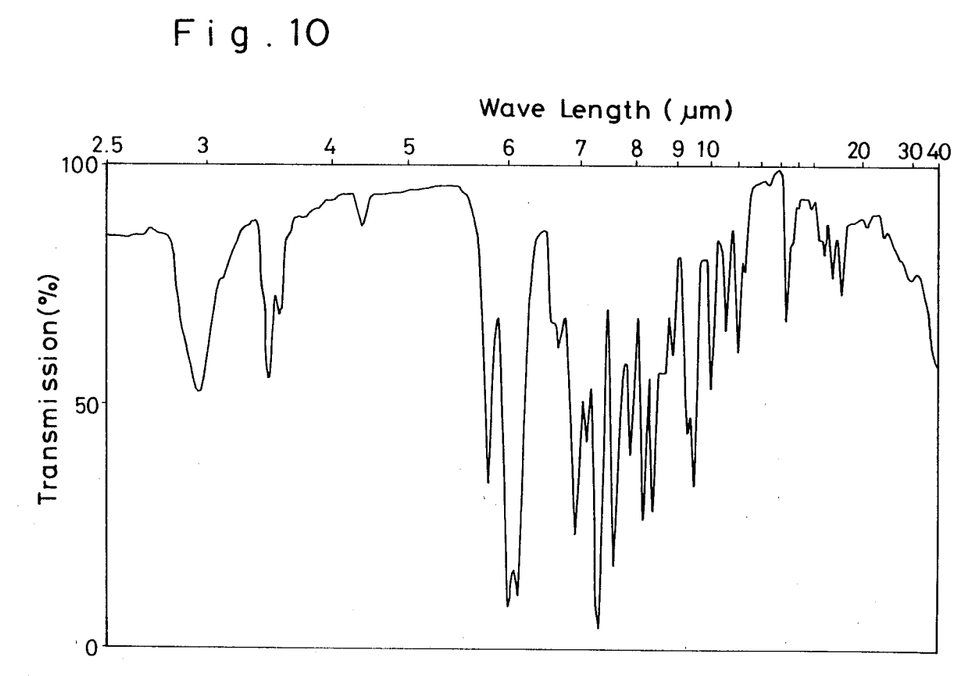

| Compound number | Structure (R, X substituents) | Melting point (°C.) | Yield (%) | Infrared absorption spectrum |
|---|---|---|---|---|
| 3 | R = H, X = N(CH₂CH₂CH₃) on ring with –N–C(=O)–N–CH₃ | 142–143 | 71 | FIG. 3 |
| 4 | R = H, X = N–CH(CH₃)₂ on ring with –N–C(=O)–N–CH₃ | 125–127 | 86 | FIG. 4 |
| 5 | R = H, X = N–CH₂CH₂CH₂CH₃ on ring with –N–C(=O)–N–CH₃ | 129–131 | 87 | FIG. 5 |
| 6 | R = H, X = N–C(CH₃)₃ on ring with –N–C(=O)–N–CH₃ | 157–159 | 88 | FIG. 6 |
| 7 | R = H, X = N–CH₂–C₆H₅ on ring with –N–C(=O)–N–CH₃ | 166–167 | 71 | FIG. 7 |
| 8 | HO–CH–CH₂–CH₂– ring with –N–C(=O)–N–CH₃ | 163–165 | 67 | FIG. 8 |
| 9 | CH₃C(=O)O–CH–CH₂–CH₂– ring with –N–C(=O)–N–CH₃ | 170–172 | 46 | FIG. 9 |
| 10 | CH₃CH₂–C(=O)O–CH–CH₂–CH₂– ring with –N–C(=O)–N–CH₃ | 123–125 | 36 | FIG. 10 |

TABLE 1-continued

Figure 11:
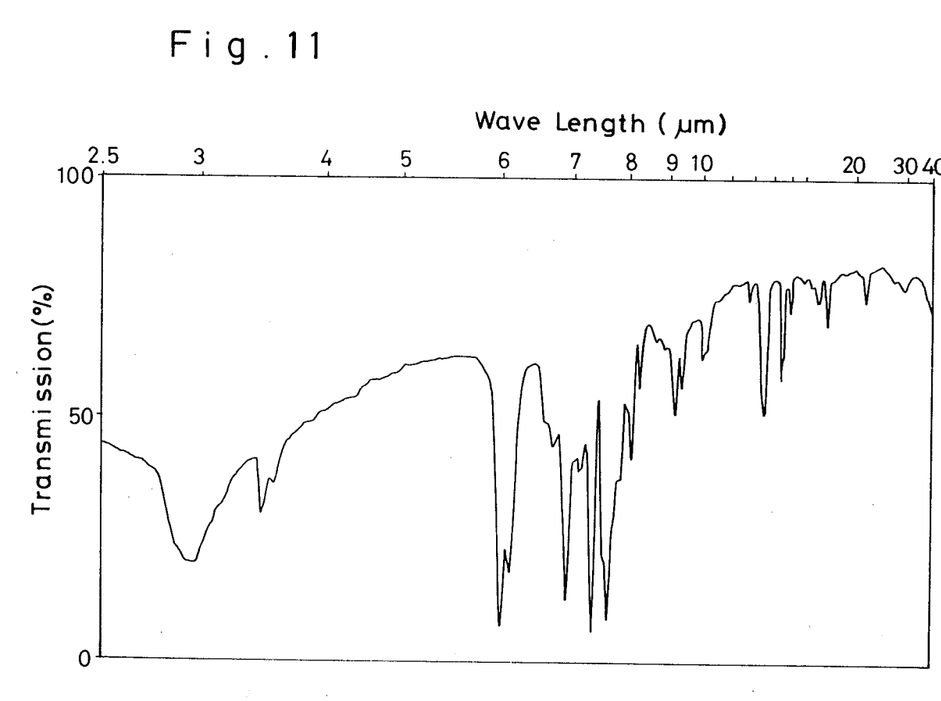

| Compound number | ![structure with R, X, N, N—CH3, O] | Melting point (°C.) | Yield (%) | Infrared absorption spectrum |
|---|---|---|---|---|
| 11 | ![structure with H, O, N, N—CH3, O] | 146–147 | 34 | FIG. 11 |

The present invention will be more precisely explained while referring to Examples as follows.

However, the present invention is not restricted to Examples under mentioned. From the foregoing description, one skilled in the art can easily ascertain the essential characteristics of the present invention, and without departing from the spirit and scope thereof, can make various changes and modifications of the invention to adapt it to various usages and conditions.

In addition, the NMR spectrum of the present compound was taken while using TMS as the internal standard and shown in Examples with the following symbols.

s means a singlet; d means a doublet; t means a triplet; 6-plet means sextet eand m means multiplet.

EXAMPLE 1

Synthesis of tetrahydro-1-(4,5,6,7-tetrahydro-5,5-dimethyl-7-oxo-2-benzothiazolyl)-3,5-dimethyl-1,3,5-triazin-2(1H)-one (Compound No. 1)

Into a solution of 3.0 g (0.012 mol) of N-(4,5,6,7-tetrahydro-5,5-dimethyl-7-oxo-2-benzothiazolyl)-N'-methylurea in 16 ml of dimethylformamide, 3.1 ml of aqueous 35% solution of formaldehyde (0.036 mol) was added, and the mixture was stirred for 30 min at room temperature. Then, 1.5 ml of aqueous 40% solution of methylamine (0.019 mol) was added to the mixture, and the whole mixture was stirred for 16 hours at room temperature and further for 3 hours at 90° C.

After distilling the solvent off from the reaction mixture, the residual solid matter was recrystallized from benzene to obtain 2.9 g of pale yellow crystals melting at 182° to 184° C. in a yield of 80%. The product showed the following IR spectrum and NMR spectrum.

IR(KBr, cm$^{-1}$): $\nu_{CO}$ 1670 and 1640.

NMR(CDCl$_3$)δ(ppm): 1.15 [6H, s, 5'—(CH$_3$)$_2$]; 2.43 and 2.79 (each 2H, each s, 4'—H and 6'—H); 2.70 (3H, s, 5—CH$_3$); 3.06 (3H, s, 3—CH$_3$); 4.37 (2H, s, 4—CH$_2$) and 5.20 (2H, s, 6—H$_2$).

EXAMPLE 2

Synthesis of tetrahydro-1-(4,5,6,7-tetrahydro-5,5-dimethyl-7-oxo-2-benzothiazolyl)-6-hydroxy-3-methyl-2(1H)-pyrimidinone (Compound No. 8)

Into 50 ml of aqueous 5% solution of sulfuric acid, 3.8 g (0.01 mol) of N-(3,3-diethoxypropyl)-N'-(4,5,6,7-tetrahydro-5,5-dimethyl-7-oxo-2-benzothiazolyl)-N-methylurea was added, and the mixture was stirred for 1 hour at 70° to 80° C. After cooling the reaction mixture, the precipitated crystals were collected by filtration, and after washing the crystals with water, the crystals were recrystallized from aqueous 50% ethanolic solution to obtain 2.0 g of white crystals melting at 163° to 165° C. in a yield of 67%. The product showed the following IR spectrum and NMR spectrum.

IR(KBr, cm$^{-1}$): $\nu_{OH}$ 3200, $\nu_{CO}$ 1640.

NMR(CDCl$_3$)δ(ppm): 1.10 [6H, s, 5'—(CH$_3$)$_2$]; 2.04–2.43 (2H, m, 5—H$_2$); 2.41 and 2.73 (each 2H, each s, 4'—H$_2$ and 6'—H$_2$); 3.10 (3H, s, 1—CH$_3$); 3.20–4.11 (2H, m, 6—H$_2$); 5.12 (1H, bs, OH) and 6.18 (1H, t, J=3 Hz, 4—H).

EXAMPLE 3

Synthesis of 6-acetoxytetrahydro-1-(4,5,6,7-tetrahydro-5,5-dimethyl-7-oxo-2-benzothiazolyl)-3-methyl 2 (1H)-pyrimidine (Compound No. 9)

Into 20 ml of pyridine, 1.0 g (0.0032 mol) of tetrahydro-1-(4,5,6,7-tetrahydro-5,5-dimethyl-7-oxo-2-benzothiazolyl)-6-hydroxy-3-methyl-2(1H)-pyrimidinone (Compound No. 8 synthesized in Example 2) was dissolved, and 0.8 g (0.01 mol) of acetyl chloride was added dropwise to the solution at 0° to 5° C. After stirring the reaction mixture for 3 hours at the temperature, the reaction mixture was poured into iced water, and extracted with chloroform. After washing the organic layer with a dilute hydrochloric acid and then with water, and drying the washed organic layer, the solvent was removed to obtain an oily substance, which was purified by silica gel chromatography to obtain 0.5 g of white crystals melting at 170° to 172° C. in a yield of 46%. The product showed the following IR spectrum and NMR spectrum.

IR(KBr, cm$^{-1}$): $\nu_{CO}$ 1730, 1670 and 1650.

NMR(CDCl$_3$)δ(ppm): 1.11 [6H, s, 5'—(CH$_3$)$_2$]; 1.98–2.52 (2H, m, 5—H$_2$); 2.09 (3H, s, OCOCH$_3$); 2.42 and 2.77 (each 2H, each s, 4'—H$_2$ and 6'—H$_2$); 3.12 (3H, s, 1—CH$_3$); 3.10–4.02 (2H, m, 6—H$_2$) and 7.49 (1H, t, J=3 Hz, 4—H).

EXAMPLE 4

Synthesis of tetrahydro-3-(4,5,6,7-tetrahydro-5,5-dimethyl-7-oxo-2-benzothiazolyl)-5-methyl-4H-1,3,5-oxadiazin-2-one (Compound No. 11)

Into 20 ml of concentrated sulfuric acid, 2.0 g (0.008 mol) of N-(4,5,6,7-tetrahydro-5,5-dimethyl-7-oxo-2-benzothiazolyl)-N'-methylurea and 1.4 g (0.016 mol) of trioxane were added, and the mixture was stirred for 10 hours at room temperature. After pouring the reaction mixture into iced water, the mixture was extracted with chloroform, and the organic layer was washed with water and dried. The solvent was removed to obtain a solid matter, which was purified by silica gel-chromatography to obtain 0.8 g of white crystals melting at 146° to 147° C. in a yield of 34%. The product showed the following IR spectrum and NMR spectrum.

IR(KBr, cm$^{-1}$): $\nu_{CO}$ 1665 and 1635.

NMR (CDCl$_3$)$\delta$(ppm): 1.10 [6H, s, 5'—(CH$_3$)$_2$]; 2.40 and 2.73 (each 2H, each s, 4'—H$_2$ and 6'—H$_2$); 3.04 (3H, s, 5—CH$_3$); 5.03 (2H, s, 6—H$_2$) and 5.70 (2H, s, 2—H$_2$).

PREPARATION EXAMPLE 1

Preparation and Application of a Wettable Powder

By mixing 50 parts by weight of the present compound (Compound No. 2), 5 parts by weight of a salt of ligninsulfonic acid, 3 parts by weight of a salt of alkylsulfonic acid and 42 parts by weight of diatomaceous earth, and pulverizing the mixture, a wettable powder was prepared.

The thus prepared wettable powder is applied after diluting thereof with water to a suitable concentration of Compound No. 2 as the active ingredient.

PREPARATION EXAMPLE 2

Preparation and Application of an Emulsifiable Concentrate

By uniformly mixing 25 parts by weight of the present compound (Compound No. 8 synthesized in Example 2), 65 parts by weight of xylene and 10 parts by weight of polyoxyethylenealkyl aryl ether, an emulsifiable concentrate was prepared.

The thus prepared emulsifiable concentrate is applied after diluting thereof with water to a suitable concentration of Compound No. 8 as the active ingredient.

PREPARATION EXAMPLE 3

Preparation and Application of a Granular composition

After uniformly mixing 8 parts by weight of the present compound (Compound No. 11 synthesized in Example 4), 40 parts by weight of bentonite, 45 parts by weight of clay and 7 parts by weight of a salt of ligninsulfonic acid, the mixture was kneaded with water and processed into granules by an extruding granulator. The granules were dried and sifted to be a product of granular composition which is directly applied.

The effectiveness of the present compounds are explained while referring to the following example of herbicidal test.

HERBICIDAL TEST EXAMPLE

To the foliage of each of the following plants grown from their seeds under a management in a plastic planter of 180×580×150 mm in size of width, length and height filled with a soil collected from an actual crop field, each of the wettable powders prepared as in Preparation Example 1 and diluted to 0.1% by weight of the active ingredient therein with water and the thus prepared aqueous suspension was sprayed by a small pressured-sprayer at a rate of 10 liters per are (100 m$^2$). After spraying the plastic planters were placed in a green house.

After 20 days of the application, the state of the plants were observed to assess the damage due to the application of each of the wettable powders, thereby finding out the herbicidal activity thereof according to the following criteria.

| Criteria of herbicidal activity | |
|---|---|
| Index | Damage (phytotoxicity) |
| 0 | none |
| 1 | very slight |
| 2 | slight |
| 3 | moderate |
| 4 | severe |
| 5 | very severe (plant withered) |
| Name of plants | |
| 1. Echinochloa crus-galli | 2. Digitaria ciliaris |
| 3. Poa annua | 4. Cyperus iria |
| 5. Chenopodium album | 6. Stellaria media |
| 7. Cardamine flexuosa | 8. Portulaca oleracea |
| 9. Glycine max (soybean) | 10. Zea mays (maize) |
| 11. Triticum aestivum (wheat) | |

The herbicidal activities of the present compounds thus assessed are shown in Table 2. The growth state of the plants when the present test was carried out was 2 to 4 leaf-stage.

TABLE 2

| | Herbicidal Activity | | | | | | | | | | | |
|---|---|---|---|---|---|---|---|---|---|---|---|---|
| | Present compound | | | | | | | | | | | |
| Plant | 1 | 2 | 3 | 4 | 5 | 6 | 7 | 8 | 9 | 10 | 11 | not applied |
| Echinochloa curs-galli | 3 | 5 | 5 | 3 | 2 | 3 | 2 | 3 | 3 | 3 | 5 | 0 |
| Digitaria ciliaris | 4 | 5 | 5 | 3 | 1 | 4 | 2 | 3 | 1 | 2 | 5 | 0 |
| Poa annua | 3 | 5 | 5 | 3 | 2 | 5 | 2 | 4 | 3 | 5 | 4 | 0 |
| Cyperus iria | 3 | 3 | 3 | 3 | 2 | 1 | 2 | 2 | 2 | 2 | 4 | 0 |
| Chenopodium album | 4 | 5 | 5 | 5 | 4 | 5 | 1 | 5 | 5 | 5 | 5 | 0 |
| Stellaria media | 5 | 5 | 5 | 5 | 5 | 5 | 3 | 5 | 4 | 4 | 5 | 0 |
| Cardamine flexuosa | 5 | 5 | 5 | 5 | 4 | 5 | 3 | 5 | 5 | 5 | 5 | 0 |
| Portulaca oleracea | 4 | 5 | 5 | 5 | 3 | 5 | 2 | 5 | 5 | 2 | 5 | 0 |
| Glycine max (soybean) | 0 | 0 | 2 | 0 | 0 | 0 | 0 | 1 | 0 | 0 | 2 | 0 |
| Zea mays (maize) | 0 | 0 | 2 | 0 | 0 | 0 | 0 | 0 | 0 | 0 | 0 | 0 |
| Triticum aestivum (wheat) | 0 | 2 | 0 | 1 | 0 | 1 | 0 | 1 | 1 | 1 | 2 | 0 |

What is claimed is:

1. A derivative of tetrahydrobenzothiazole, represented by the formula (I):

(I)

[Structural formula showing a tetrahydrobenzothiazole derivative with CH$_3$, CH$_3$ groups, N-R, X, N-CH$_3$, S, and two O groups]

wherein R represents a hydrogen atom, a hydroxyl group or a lower-acyloxy group selected from acetoxy group and propionyloxy group and X represents a methylene group, a C$_1$ to C$_4$-alkylamino group, a benzylamino group or —O—.

2. Tetrahydro-1-(4,5,6,7-tetrahydro-5,5-dimethyl-7-oxo-2-benzothiazolyl)-3,5-dimethyl-1,3,5-triazine-2(1H)-one, represented by the formula:

3. Tetrahydro-1-(4,5,6,7-tetrahydro-5,5-dimethyl-7-oxo-2-benzothiazolyl)-3-methyl-5-propyl-1,3,5-triazin-2(1H)-one, represented by the formula:

4. Tetrahydro-1-(4,5,6,7-tetrahydro-5,5-dimethyl-7-oxo-2-benzothiazolyl)-3-methyl-5-isopropyl-1,3,5-triazin-2(1H)-one, represented by the formula:

5. Tetrahydro-3-(4,5,6,7-tetrahydro-5,5-dimethyl-7-oxo-2-benzothiazolyl)-5-methyl-4(H)-1,3,5-oxadiazin-4-one, represented by the formula:

6. A herbicidal composition comprising as an active ingredient a herbicidally effective amount of at least one derivative of tetrahydrobenzothiazole, represented by the formula (I):

wherein R represents a hydrogen atom, a hydroxyl-, acetoxy- or propionyloxy group and X represents a methylene-, C$_1$ to C$_4$-alkylamino- or benzylamino group or —O—, and a diluent therefor.

7. A herbicidal composition according to claim 6, wherein said derivative is tetrahydro-1-(4,5,6,7-tetrahydro-5,5-dimethyl-7-oxo-2-benzothiazolyl)-3,5-dimethyl-1,3,5-triazin-2(1H)-one, represented by the formula:

8. A herbicidal composition according to claim 6, wherein said derivative is tetrahydro-1-(4,5,6,7-tetrahydro-5,5-dimethyl-7-oxo-2-benzothiazolyl)-3-methyl-5-propyl-1,3,5-triazin-2(1H)-one, represented by the formula:

9. A herbicidal composition according to claim 6, wherein said derivative is tetrahydro-1-(4,5,6,7-tetrahydro-5,5-dimethyl-7-oxo-2-benzothiazolyl)-3-methyl-5-isopropyl-1,3,5-triazin-2(1H)-one, represented by the formula:

10. A herbicidal composition according to claim 6, wherein said derivative is tetrahydro-3-(4,5,6,7-tetrahydro-5,5-dimethyl-7-oxo-2-benzothiazolyl)-5-methyl-4(H)-1,3,5-oxadiazin-4-one, represented by the formula:

* * * * *